(12) United States Patent
Yamazaki

(10) Patent No.: US 8,444,552 B2
(45) Date of Patent: May 21, 2013

(54) ENDOSCOPE

(75) Inventor: Masayuki Yamazaki, Saitama (JP)

(73) Assignee: Fujifilm Corporation, Tokyo (JP)

( * ) Notice: Subject to any disclaimer, the term of this patent is extended or adjusted under 35 U.S.C. 154(b) by 560 days.

(21) Appl. No.: 12/693,160

(22) Filed: Jan. 25, 2010

(65) Prior Publication Data

US 2010/0191058 A1    Jul. 29, 2010

(30) Foreign Application Priority Data

Jan. 26, 2009    (JP) .............................. P2009-014253

(51) Int. Cl.
*A61B 1/00*    (2006.01)

(52) U.S. Cl.
USPC ............ 600/141; 600/139; 600/142; 600/146

(58) Field of Classification Search
USPC .................. 600/129, 130, 139, 141, 142, 146
See application file for complete search history.

(56) References Cited

U.S. PATENT DOCUMENTS

| 4,108,211 A | 8/1978 | Tanaka |
| 6,482,149 B1 | 11/2002 | Torii |
| 6,641,528 B2 * | 11/2003 | Torii ............................. 600/142 |

FOREIGN PATENT DOCUMENTS

| DE | 100 23 392 A1 | 2/2000 |
| JP | 2000-316800 | 11/2000 |
| JP | 2000-316800 A | 11/2000 |
| JP | 3835077 | 8/2006 |

OTHER PUBLICATIONS

European Search Report dated Jun. 11, 2010.
Japanese Office Action dated Jan. 29, 2013 with partial English translation thereof.

* cited by examiner

*Primary Examiner* — Matthew J Kasztejna
*Assistant Examiner* — Kevin G Barry, III
(74) *Attorney, Agent, or Firm* — McGinn IP Law Group, PLLC

(57) ABSTRACT

An endoscope includes a manipulation unit, and an insertion unit which is disposed in continuation to the manipulation unit. The insertion unit contains a bending portion which has a plurality of articulation wheels coupled in succession, two adjacent ones of the articulation wheels being coupled by a shaft member so as to be relatively turnable around the shaft member which crosses the center axis of the bending portion, the bending portion being bent in such a way that a wire which leads to the manipulation unit via the plurality of articulation wheels is tractively manipulated. The shaft member has a guide part formed with an insertional hole through which the wire is inserted, and at least the guide part of the shaft member is turnable around the center axis of the shaft member, to both the two articulation wheels coupled by the shaft member.

6 Claims, 6 Drawing Sheets

ENDOSCOPE

CROSS-REFERENCE TO RELATED APPLICATIONS

This application claims the benefit of Japanese Patent Application No. 2009-014253, filed on Jan. 26, 2009, the entire contents of which are hereby incorporated by reference, the same as if set forth at length; the entire of which are incorporated herein by reference.

BACKGROUND OF THE INVENTION

1. Technical Field

The present invention relates to an endoscope.

2. Description of Related Art

An endoscope is typically furnished with a manipulation unit, and an insertion unit which is disposed in continuation to the manipulation unit. The insertion unit includes a bending portion, and a distal end portion which is provided in continuation to the distal end side of the bending portion. The distal end portion is provided with an imaging apparatus including a solid-state imaging element, an illuminating optical system, etc., and it images the part tobe-observed of a subject. The bending portion has a plurality of articulation wheels which are coupled in succession, and the two adjacent ones of which are coupled by a pin orthogonal to a center axis of the bending portion, so as to be relatively turnable around the pin. In addition, a wire which leads to the manipulation unit via the articulation wheels is laid. The wire is tractively manipulated, whereby the bending portion is bent, and the distal end portion is deflected in a predetermined direction.

In the endoscope wherein the distal end portion is deflected in the four directions of upward and downward directions and rightward and leftward directions, a pin which couples the two adjacent articulation wheels is arranged so as to alternately extend in a first direction orthogonal to the center axis of the bending portion, and a second direction orthogonal to the center axis of the bending portion and also orthogonal to the first direction. Besides, four wires are laid along the center axis of the bending portion at intervals of about 90 degrees around this center axis. Insertional holes which penetrate in the axial direction of the bending portion are formed at the distal end parts of the pin, and the respective wires are disposed so as to successively pass through the insertional holes of the pin arrayed in the axial direction of the bending portion.

The coupling place between the two adjacent articulation wheels is configured in such a manner that coupling parts provided in both the articulation wheels are placed one over the other double inside and outside, and that the pin is inserted through pin holes which are respectively formed in both the coupling parts. The pin is caulked to the coupling part of one articulation wheel located outside, and it is secured to this coupling part. On the other hand, the pin is loosely fitted in the coupling part of the other articulation wheel located inside. Therefore, the other adjacent articulation wheel turns around the pin relative to one articulation wheel to which the pin is secured (refer to, for example, JP-3835077-B).

In the endoscope of the structure of JP-3835077-B stated above, when the two adjacent articulation wheels have been relatively turned, the inflection of the wire hardly occurs at the edge of the insertional hole facing to one articulation wheel to which the pin is secured, but a conspicuous inflection can correspondingly occur in the wire at the edge of the insertional hole facing to the other articulation wheel. Therefore, a force which acts on the wire by the touch thereof with the pin concentrates on that part of the pin which touches the edge of one of the insertional holes, and the wear of the wire at the part becomes conspicuous.

SUMMARY

The present invention has been made in view of the above circumstances, and has for its object to provide an endoscope in which the wear of a wire for bending a bending portion is suppressed.

An endoscope includes a manipulation unit and an insertion unit. The insertion unit is disposed in continuation to the manipulation unit and includes a bending portion. In the bending portion, the insertion unit includes a plurality of articulation wheels and a plurality of shaft members. The plurality of articulation wheels are coupled in succession. Each shaft member includes a guide part formed with an insertional hole through which a wire is inserted. Two adjacent ones of the plurality of articulation wheels are coupled by the shaft member so as to be relatively turnable around the shaft member on an direction crossing a center axis of the bending portion. The bending portion is bent in such a way that the wire which leads to the manipulation unit via the plurality of articulation wheels is tractively manipulated. At least each guide part of the shaft member is turnable around a center axis of each shaft member, to both the two articulation wheels which are coupled by the shaft member.

According to the present invention, a force which acts on a wire by the touch of a shaft member with a guide portion is distributed, whereby the wear of the wire can be suppressed.

DETAILED DESCRIPTION OF EMBODIMENTS OF THE INVENTION

Figure 1:
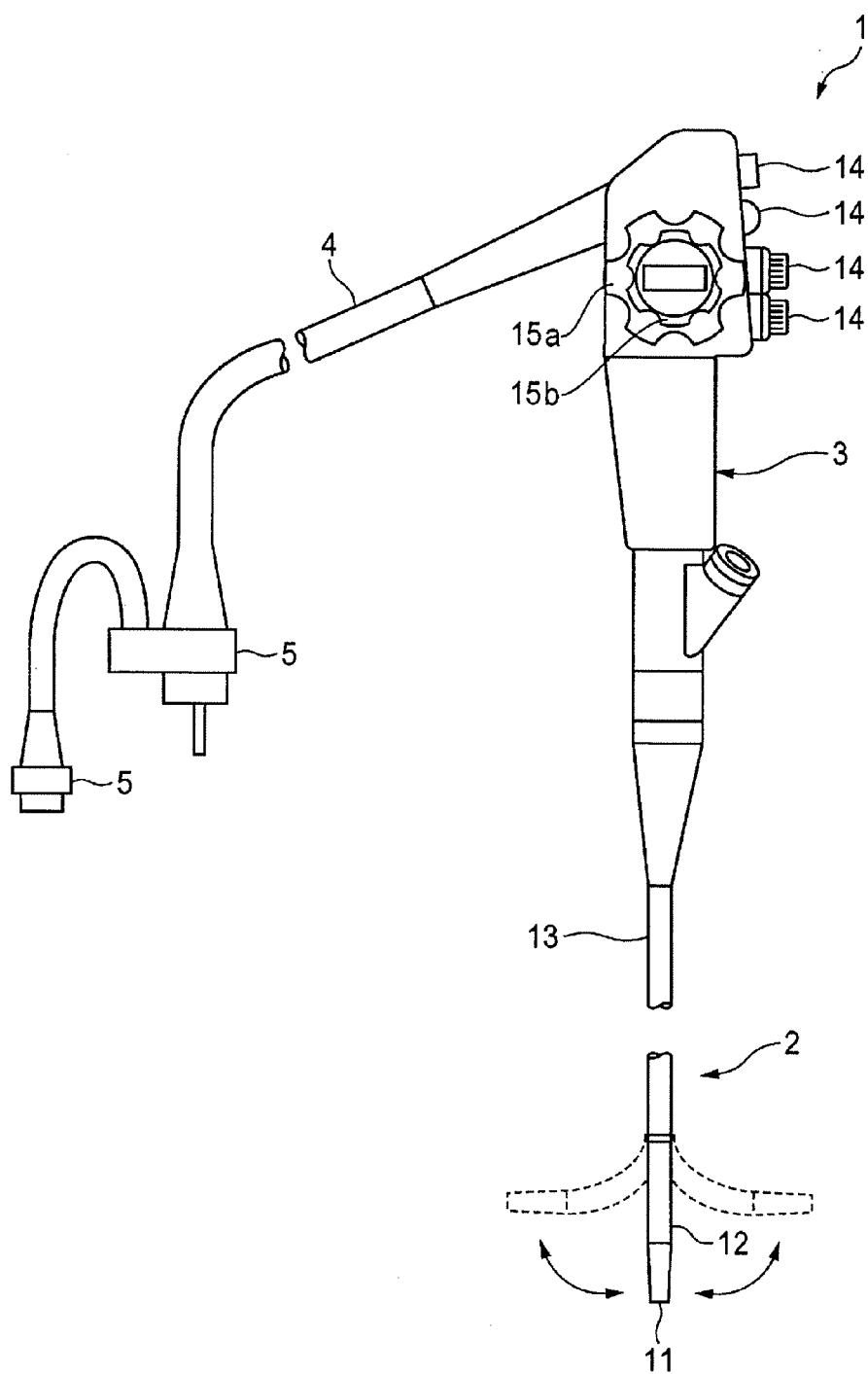
FIG. 1 is a plan view showing an example of an endoscope for explaining an embodiment of the present invention.
Figure 2:
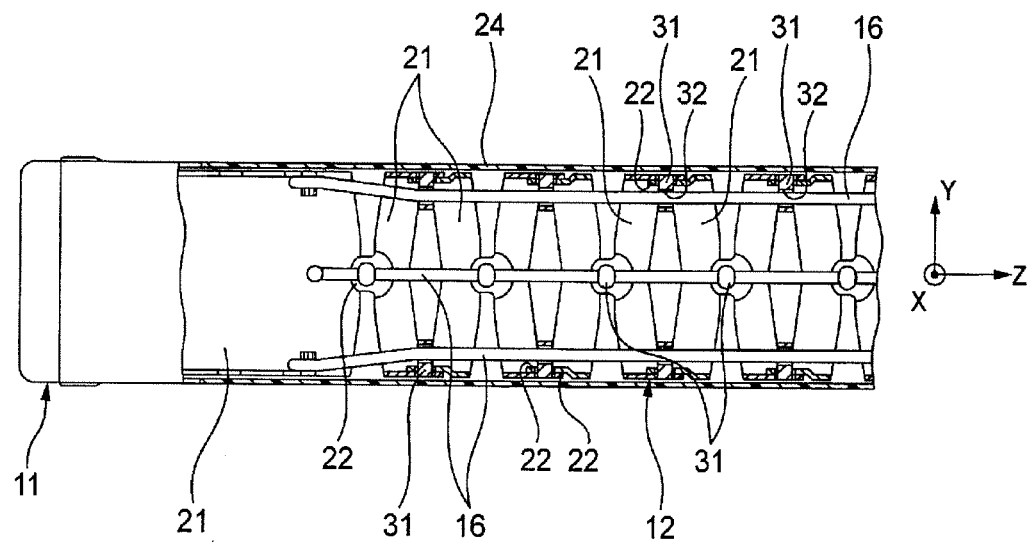
FIG. 2 is a sectional view of a bending portion which is included in the insertion unit of the endoscope shown in FIG. 1.
Figure 3:
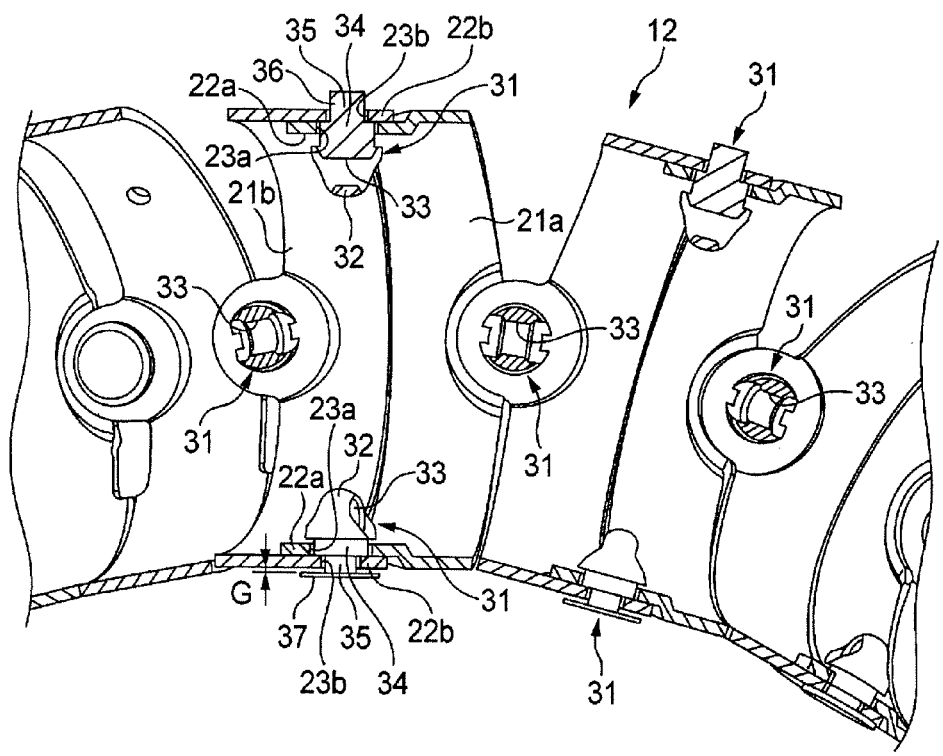
FIG. 3 is a sectional view enlargedly showing the bending portion in FIG. 2, and showing an example of a shaft member which couples the two adjacent articulation wheels of the bending portion.

Now, a embodiment of the present invention will be described with reference to the drawings. FIG. 1 is a plan view showing an example of an endoscope for explaining the embodiment of the present invention, FIG. 2 is a sectional view of a bending portion which is included in the insertion unit of the endoscope in FIG. 1, and FIG. 3 is a sectional view enlargedly showing the bending portion in FIG. 2.

As shown in FIG. 1, the endoscope 1 includes a manipulation unit 3, an insertion unit 2 which is disposed in continuation to the manipulation unit 3 and which is inserted into a subject, and a universal cable 4 which extends from the manipulation unit 3. The universal cable 4 contains a light guide, a signal line, etc. not shown, and it is connected to a light source device, a signal processing device, etc. not shown, in a connector 5 which is disposed at its tail end.

The insertion unit 2 includes a bending portion 12, a distal end portion 11

The insertion unit 2 includes a bending portion 12, a distal end portion 11 which is disposed in continuation to the distal end side of the bending portion 12, and a flexible soft portion 13 which is disposed in continuation to the base end side of the bending portion 12. The bending portion 12 is coupled to the manipulation unit 3 through the soft portion 13. The light guide and the signal line arrive at the distal end portion 11 via the manipulation unit 3, the soft portion 13 and the bending portion 12.

A solid-state imaging element, for example, a CCD image sensor is disposed in the distal end portion 11. Besides, a plurality of buttons 14 for controlling imaging by the solid-state imaging element of the distal end portion 11, etc., and knobs 15a and 15b for manipulating the bending of the bending portion 12, are disposed in the manipulation unit 3.

Illumination light generated by the light source device is guided to the distal end portion 11 through the light guide, and it is projected on the subject. In addition, reflection light reflected from the subject is focused on the solid-state imaging element included in the distal end portion 11, whereby the image signal of the subject is generated. This image signal is sent to the signal processing device through the signal line. The signal processing device generates display image data by processing, for example, the inputted image signal, and it displays a subject image based on the generated display image data, on a monitor (not shown).

As shown in FIG. 2, the bending portion 12 has a plurality of articulation wheels 21 which are coupled in succession. Each of the articulation wheels 21 is a hard member which is formed into a substantially cylindrical shape. The articulation wheel 21 which forms one end of the array of these articulation wheels 21 is joined unitarily with the rear end part of the outer shell of the distal end portion 11. Incidentally, the outer shell of the distal end portion 11 and the plurality of articulation wheels 21 of the bending portion 12 are both covered with a flexible tube 24 such as rubber tube.

Two of the articulation wheels 21 adjacent to each other are coupled by a shaft member 31 so as to be relatively turnable around the shaft member 31 on a direction crossing a center axis of the bending portion 12. The shaft members 31 are arranged so that their center axes may alternately extend in a first direction X which is orthogonal to the center axis Z of the bending portion 12, and a second direction Y which is orthogonal to the center axis of the bending portion 12 and which is also orthogonal to the first direction X.

In addition, four wires 16 (one of which is not shown) are laid along the center axis of the bending portion 12 at intervals of about 90 degrees around this center axis. Insertional holes 32 which penetrate in a diametric direction are formed in those end parts of the shaft members 31 which protrude on the inside diameter sides of the articulation wheels 21, and each of the wires 16 is disposed by successively passing through the insertional holes 32 of the shaft members 31 arrayed in the axial direction of the bending portion 12.

One end part of each wire 16 is secured by welding or the like appropriate means to the articulation wheel 21 which is joined unitarily with the outer shell of the distal end portion 11. Besides, the other end part of each wire 16 is connected to the knob 15a or 15b of the manipulation unit 3. By way of example, one set of wires 16 which vertically oppose with the center axis of the bending portion 12 interposed therebetween in FIG. 2 correspond to the vertical bending (upward or downward bending) of the bending portion 12, and they are respectively connected to the knob 15a. In addition, the remaining set of wires 16 which horizontally oppose with the center axis of the bending portion 12 interposed therebetween correspond to the horizontal bending (rightward or leftward bending) of the bending portion 12, and they are respectively connected to the knob 15b.

With the rotating manipulation of the knob 15a, either of the set of wires 16 connected thereto is drawn, whereby the bending portion 12 is bent upwards or downwards. Besides, with the rotating manipulation of the knob 15b, either of the set of wires 16 connected thereto is drawn, whereby the bending portion 12 is bent rightwards or leftwards. The upward and downward bendings of the bending portion 12 responsive to the rotating manipulations of the knob 15a, and the rightward and leftward bendings of the bending portion 12 responsive to the rotating manipulations of the knob 15b are combined, whereby the distal end portion 11 is deflected in the four directions of upward and downward directions and rightward and leftward directions.

Next, the coupling place between the two adjacent articulation wheels 21 will be described in detail.

First, except in the articulation wheels 21 which form the ends of the array of the plurality of articulation arrays 21, a pair of coupling parts 22 opposing to each other are respectively disposed at both the axial end parts of each articulation wheel 21. In each of the articulation wheels 21 which form the ends of the array of the plurality of articulation wheels 21, a pair of coupling parts 22 are disposed at only the end part of the articulation wheel on the side thereof on which the other articulation wheel 21 is coupled.

In addition, as shown in FIG. 3, regarding the two adjacent articulation wheels, the coupling part 22b of the other articulation wheel 21b is placed on the coupling part 22a of one articulation wheel 21a double inside and outside. The coupling part 22a located inside and the coupling part 22b located outside are respectively formed with shaft holes 23a and 23b through which the shaft member 31 is inserted. The shaft hole 23b of the coupling part 22b located outside is formed to be smaller in diameter than the shaft hole 23a of the coupling part 22a located inside. The shaft member 31 is inserted through the respective shaft holes 23a and 23b of both the coupling parts 22a and 22b placed one over the other, whereby both the articulation wheels 21a and 21b are coupled.

The shaft member 31 includes a guide part 32 which is formed with an insertional hole 33 for inserting the wire 16 therethrough, a first shaft part 34 which extends from the guide part 32, and a second shaft part 35 which is provided in continuation to the distal end of the first shaft part 34 and coaxially with the first shaft part 34. By the way, in FIG. 3, among the shaft members 31 juxtaposed as the three rows of upper, middle and lower rows, the shaft member 31 of the upper row is shown in section, and the shaft member 31 of the middle row is shown with its guide part 32 partially broken away so as to expose the insertional hole 33.

The first shaft part 34 is formed to be slightly smaller in diameter than the shaft hole 23a of the coupling part 22a located inside, and it is loosely fitted in the shaft hole 23a. In addition, the first shaft part 34 is formed to be larger in diameter than the shaft hole 23b of the coupling part 22b located outside, and it is held in engagement with the peripheral edge part of the shaft hole 23b at its end face.

The second shaft part 35 is formed to be slightly smaller in diameter than the shaft hole 23b of the coupling part 22b located outside, and it is loosely fitted in the shaft hole 23b. In addition, the distal end part of the second shaft part 35 protrudes out of the coupling part 22b through the shaft hole 23b. The distal end part 36 protruding out of the coupling part 22b is plastically deformed into the shape of a flat disc so as to become larger in diameter than the shaft hole 23b, and it is made a nip part 37. Incidentally, among the shaft members 31 juxtaposed in the three rows of upper, middle and lower rows shown in FIG. 3, the shaft member at the upper row illustrates a state before the distal end part 36 is plastically deformed, and the shaft member at the lower row illustrates a state where the distal end part 36 has been plastically deformed to form the nip part 37.

The shaft member 31 formed with the nip part 37 is mounted on the coupling part 22b in such a manner that the peripheral edge part of the shaft hole 23b of the coupling part 22b is pinched in a direction in which both the coupling parts 22a and 22b are placed one over the other, between the first shaft part 34 and the nip part 37. That is, the first shaft part 34 forms a nip part which pairs with the nip part 37.

Here, a slight gap G is provided in the direction in which both the coupling parts 22a and 22b are placed one over the other, between the first shaft part 34 and the nip part 37 which function as the pair of nip parts of the shaft member 31 and the coupling part 22b which is pinched between the parts 34 and 37. The first shaft part 34 is loosely fitted into the shaft hole 23a of the coupling part 22a, the second shaft part 35 is loosely fitted into the shaft hole 23b of the coupling part 22b, and the gap G is provided, whereby the shaft member 31 can rotate on its own axis, without being secured by either of the articulation wheels 21a and 21b.

Figure 4:
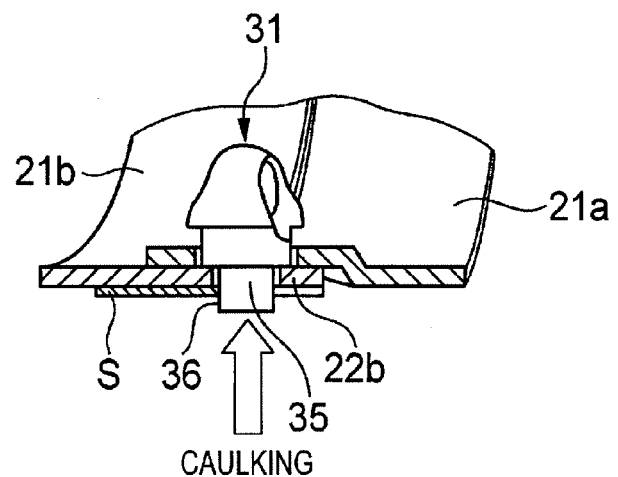
FIG. 4 is a sectional view showing an example of the mounting of the shaft member.
Figure 4:
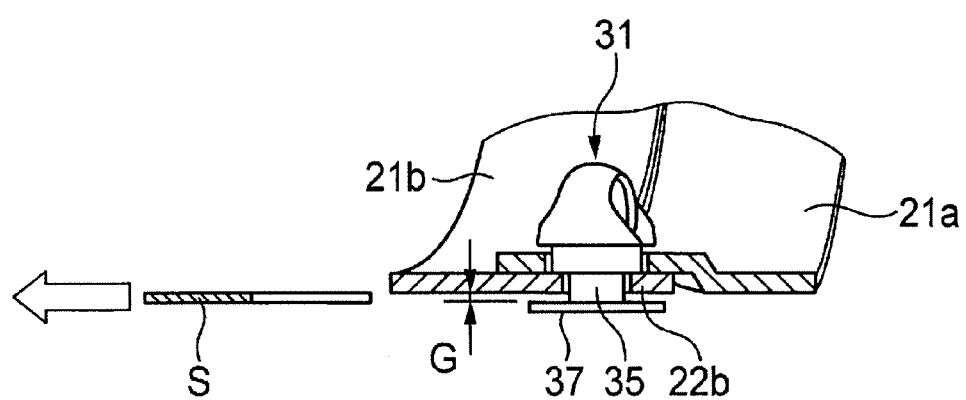

The distal end part 36 of the second shaft part 35 is plastically deformed by, for example, caulking, thereby to be made the nip part 37. Here, as shown in FIG. 4, the distal end part 36 is caulked with a metal sheet or the like spacer S put on the coupling part 22b, and the spacer S is removed after the caulking, whereby the above gap G can be easily provided.

In this manner, the whole shaft member 31 including the guide part 32 can rotate on its own axis, that is, it can turn to either of the articulation wheels 21a and 21b around its center axis. Moreover, both the articulation wheels 21a and 21b are relatively turnable around the center axis of the shaft member 31.

Next, the deformation of the wire 16 with the bending of the bending portion 12 will be described with reference to FIGS. 5A and 5B.

Figure 5A:
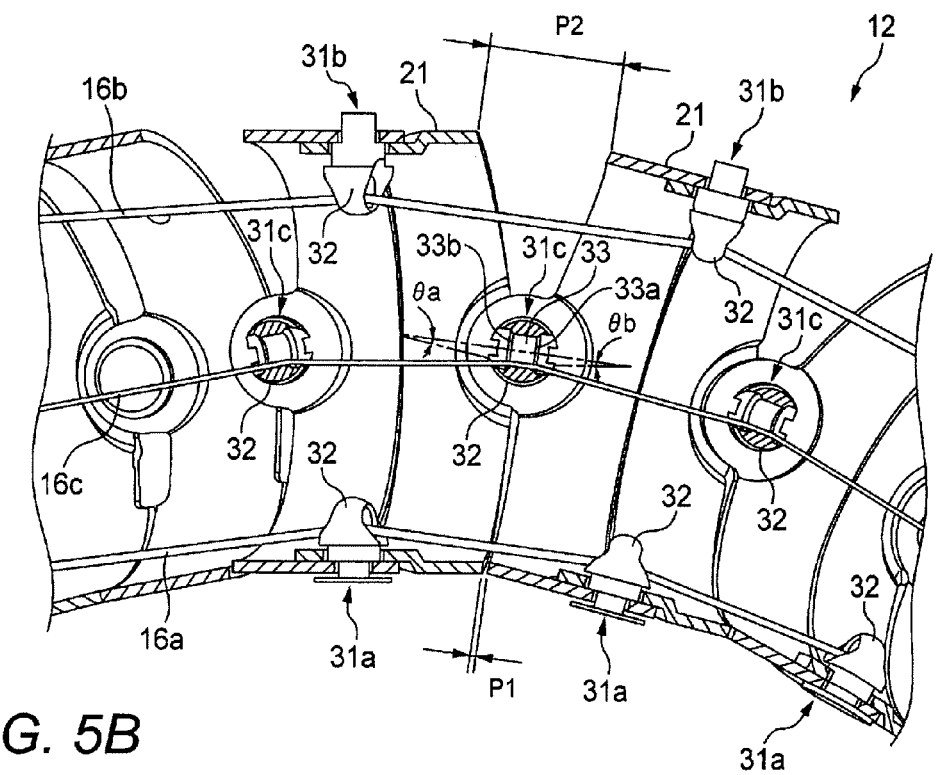
FIGS. 5A and 5B are sectional views showing the operation of the bending portion of the endoscope shown in FIG. 1.

FIG. 5A shows the state of the bending portion 12 in the case where the wire 16a disposed at the lower part of the bending portion 12 in the figure has been drawn. When the wire 16a is drawn, the two adjacent articulation wheels 21 coupled by the shaft members 31c juxtaposed at the side part of the bending portion 12 are relatively turned in a sense in which an interval P1 at the lower edges of these articulation wheels 21 is narrowed, so as to shorten the path length of the wire 16a stipulated by the guide parts 32 of the shaft members 31a juxtaposed at the lower part of the bending portion 12. Thus, the bending portion 12 is bent downwards. Incidentally, an interval P2 at the upper edges of both the articulation wheels 21 is widened, the path length of the wire 16b stipulated by the guide parts 32 of the shaft members 31b juxtaposed at the upper part of the bending portion 12 is consequently lengthened, and the wire 16b is responsively delivered from the manipulation unit 3.

The wire 16c which is disposed at the side part of the bending portion 12 while being successively inserted through the insertional holes 33 that are formed in the guide parts 32 of the shaft members 31c juxtaposed at the side part of the bending portion 12, is appropriately inflected at the positions of the respective shaft members 31c in accordance with the bending of the bending portion 12. Concretely, the wire 16c touches the edges 33a and 33b of the guide part 32 corresponding to both the ends of the insertional hole 33, and it is appropriately inflected at the edges 33a and 33b.

Here, the whole shaft member 31c including the guide part 32 can turn to either of the two coupled articulation wheels 21. The wire 16c touches the edges 33a and 33b of the guide part 32, respectively, and it gives the shaft member 31c torques around the center axis thereof. Accordingly, the shaft member 31c is turned round its center axis so that the torque exerted by the touch with the wire 16c at one edge 33a may balance with the torque exerted by the touch with the wire 16c at the other edge 33b.

Owing to the turning of the shaft member 31c, the inflection angle θa of the wire 16c at one edge 33a of the guide part 32 and the inflection angle θb of the wire 16c at the other edge 33b become substantially equal. In addition, a force exerted on the wire 16c by the touch with the guide part 32 is distributed substantially equally to the part of the wire 16c touching one edge 33a and the part thereof touching the other edge 33b.

Figure 5B:
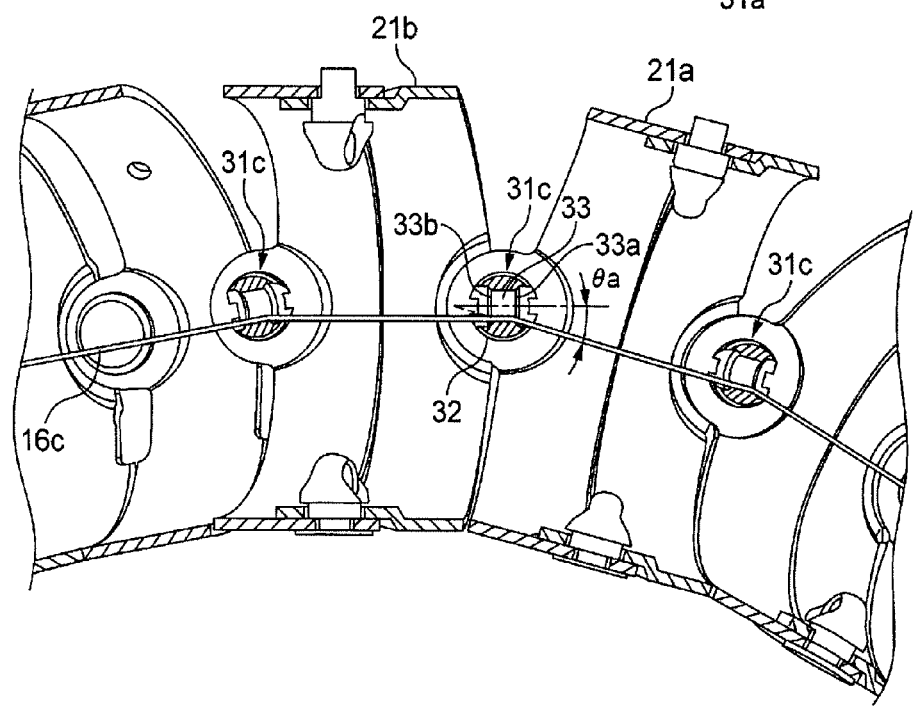

For reference, FIG. 5B illustrates a case where the shaft member coupling the two adjacent articulation wheels has been secured to one articulation wheel, that is, a case where the shaft member including the guide part is unturnable to one articulation wheel.

The shaft member 31c couples the two adjacent articulation wheels 21a and 21b, and it is secured to one articulation wheel 21b. The inflection of the wire 16c hardly occurs at the edge 33b of the guide part 32 facing to the articulation wheel 21b to which the shaft member 31c is secured. However, a conspicuous inflection appears in the wire 16c (θa>>θb≈0) to a corresponding extent, at the edge 33a facing to the other articulation wheel 21a. Therefore, the force exerted on the wire 16c by the touch of the shaft member 31c with the guide part 32 concentrates on the part touching one edge 33a.

In this manner, the whole shaft member 31 including the guide part 32 is turnable to both the two articulation wheels 21 to-be-coupled around its center axis, so that when both the articulation wheels 21 have been relatively turned, the wire can be equally inflected at both the edges of the guide part 32. Thus, the force exerted on the wire 16 by the touch with the guide part 32 can be distributed, and the wear of the wire 16 can be suppressed.

Figure 6:
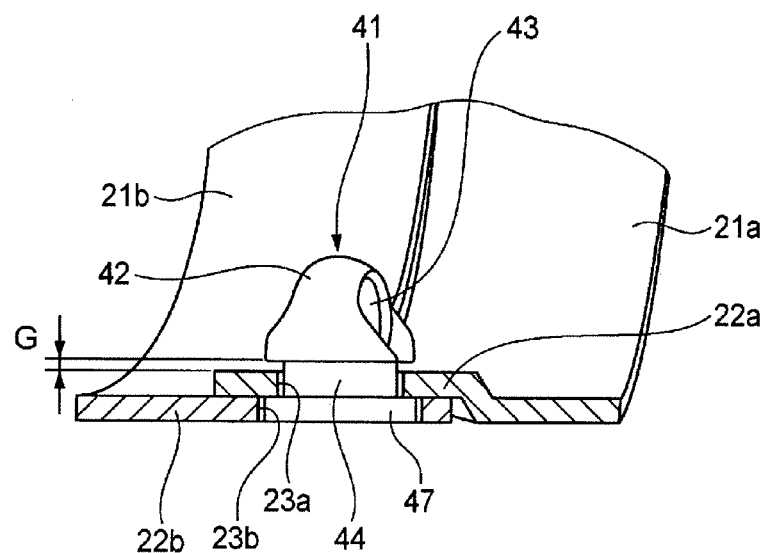
FIG. 6 is a sectional view showing a modification of the shaft member.
Figure 7:
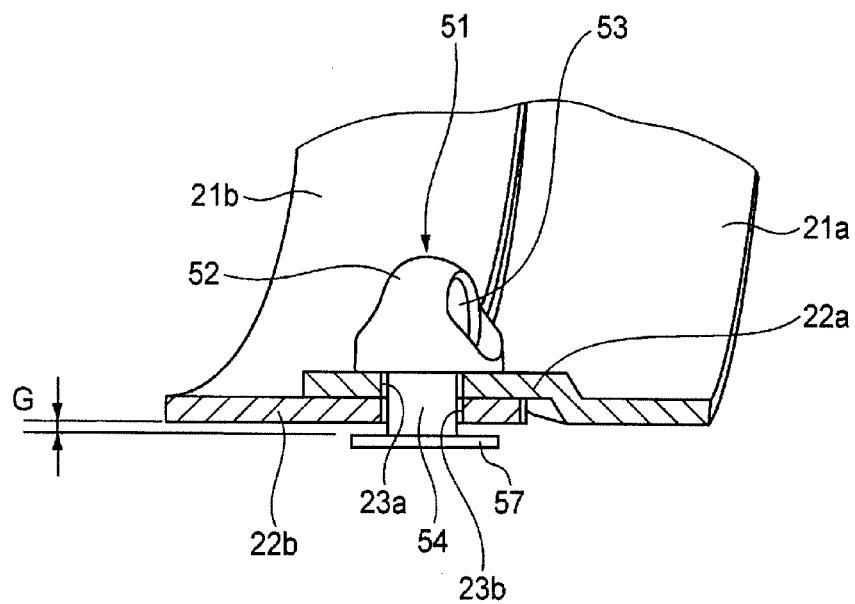
FIG. 7 is a sectional view showing a modification of the shaft member.
Figure 8:
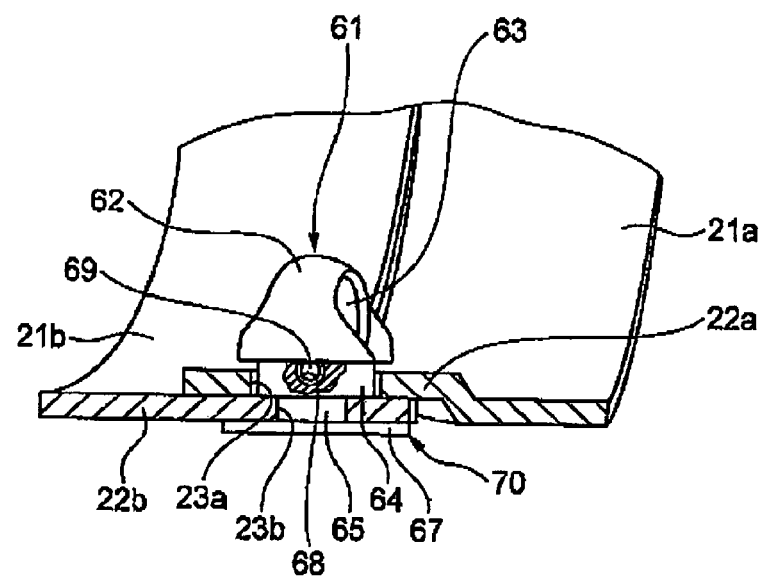
FIG. 8 is a sectional view showing a modification of the shaft member.

FIGS. 6 through 8 show modifications of the shaft member which couples the two adjacent articulation wheels 21 of the bending portion 12.

The shaft member 31 stated above is mounted on the coupling part 22b located outside, in the respective coupling parts 22a and 22b of the two adjacent articulation wheels 21a and 21b as are placed one over the other, in such a manner that the coupling part 22b is pinched between the pair of nip parts 34 and 37. In contrast, the shaft member 41 shown in FIG. 6 is mounted on the coupling part 22a located inside, in such a manner that the coupling part 22a is pinched.

The shaft hole 23a of the coupling part 22a located inside is formed to be smaller in diameter than the shaft hole 23b of the coupling part 22b located outside. The shaft member 41 includes a guide part 42 formed with an insertional hole 43 through which the wire 16 is inserted, and a shaft part 44 extended from the guide part 42.

The guide part 42 is formed to be larger in diameter than the shaft hole 23a of the coupling part 22a located inside. The shaft part 44 is formed to be slightly smaller in diameter than the shaft hole 23a, and it is loosely fitted into the shaft hole 23a. In addition, the distal end part of the shaft part 44 protrudes out of the coupling part 22a through the shaft hole 23a.

The distal end part protruding from the coupling part 22a is plastically deformed into the shape of a flat disc so as to become larger in diameter than the shaft hole 23a and slightly smaller in diameter than the shaft hole 23b of the coupling part 22b located outside, thereby to be made a nip part 47.

The shaft member 41 formed with the nip part 47 is mounted on the coupling part 22a in such a manner that the peripheral edge part of the shaft hole 23a of the coupling part 22a is pinched in a direction in which both the coupling parts 22a and 22b are placed one over the other by the guide part 42 and the nip part 47. That is, the guide part 42 forms a nip part which pairs with the nip part 47. Besides, the nip part 47 is slightly smaller in diameter than the shaft hole 23b of the coupling part 22b located outside, and it is loosely fitted into the shaft hole 23b of the coupling part 22b located outside, thereby to function also as a shaft for the coupling part 22b.

In addition, a slight gap G is provided in the direction in which both the coupling parts 22a and 22b are placed one over the other, between the guide part 42 and the nip part 47 which form the pair of nip parts of the shaft member 41 and the coupling part 22a which is pinched between these parts 42 and 47. The shaft part 44 is loosely fitted into the shaft hole 23a of the coupling part 22a, the nip part 47 of the shaft part 44 is loosely fitted into the shaft hole 23b of the coupling part 22b, and the gap G is provided, whereby the shaft member 41 can rotate on its own axis without being secured to either of the articulation wheels 21a and 21b.

The above gap G can be provided in such a way, for example, that a metal sheet or the like spacer is interposed between the guide part 42 and the coupling part 22a, that the distal end part of the shaft part 44 is caulked, and that the spacer is removed after the caulking.

In this manner, the whole shaft member 41 including the guide part 42 is turnable to both the two articulation wheels 21 to-be-coupled around its center axis, so that when both the articulation wheels 21 have been relatively turned, the wire can be equally inflected at both the edges of the guide part 42. Thus, a force exerted on the wire 16 by the touch with the guide part 42 can be distributed, and the wear of the wire 16 can be suppressed.

The shaft member 51 shown in FIG. 7 is mounted pinching both the respective coupling parts 22a and 22b of the two adjacent articulation wheels 21a and 21b as are placed one over the other.

The shaft holes 23a and 23b of both the coupling parts 22a and 22b are formed at an identical diameter. The shaft member 51 includes a guide part 52 formed with an insertional hole 53 through which the wire 16 is inserted, and a shaft part 54 extended from the guide part 52.

The guide part 52 is formed to be larger in diameter than the shaft holes 23a and 23b of both the coupling parts 22a and 22b. The shaft part 54 is formed to be slightly smaller in diameter than the shaft holes 23a and 23b, and it is loosely fitted into the shaft holes 23a and 23b. In addition, the distal end part of the shaft part 54 protrudes out of the coupling part 22b through the shaft holes 23a and 23b. The distal end part protruding from the coupling part 22b is plastically deformed into the shape of a flat disc so as to become larger in diameter than the shaft hole 23b, thereby to be made a nip part 57.

The shaft member 51 formed with the nip part 57 is mounted in such a manner that the peripheral edge part of the shaft holes 23a and 23b of the coupling parts 22a and 22b are pinched in a direction in which both the coupling parts 22a and 22b are placed one over the other, between the guide part 52 and the nip part 57. That is, the guide part 52 forms a nip part which pairs with the nip part 57.

In addition, a slight gap G is provided in the direction in which both the coupling parts 22a and 22b are placed one over the other, between the guide part 52 and the nip part 57 which form the pair of nip parts of the shaft member 51 and both the coupling parts 22a and 22b which are pinched between these parts 52 and 57. The shaft part 54 is loosely fitted into the shaft holes 23a and 23b of both the coupling parts 22a and 22b, and the gap G is provided, whereby the shaft member 51 can rotate on its own axis without being secured to either of the articulation wheels 21a and 21b.

The above gap G can be provided in such a way, for example, that the distal end part of the shaft part 54 is caulked with a spacer interposed between the guide part 52 and the coupling part 22a, or with a spacer put on the coupling part 22b, and that the spacer is removed after the caulking.

In this manner, the whole shaft member 51 including the guide part 52 is turnable to both the two articulation wheels 21 to-be-coupled around its center axis, so that when both the articulation wheels 21 have been relatively turned, the wire can be equally inflected at both the edges of the guide part 52. Thus, a force exerted on the wire 16 by the touch with the guide part 52 can be distributed, and the wear of the wire 16 can be suppressed.

Next, reference will be had to FIG. 8. Although the above shaft member 31 has the configuration in which the whole shaft member including the guide part 32 is turnable to the two articulation wheels 21 to-be-coupled, a shaft member 61 shown in FIG. 8 has a configuration in which only a guide part 62 is turnable.

The shaft hole 23b of a coupling part 22b located outside, in the respective coupling parts 22a and 22b of the two adjacent articulation wheels 21a and 21b as are placed one over the other, is formed to be smaller in diameter than the shaft hole 23a of the coupling part 22a located inside.

The shaft member 61 includes the guide part 62 formed with an insertional hole 63 through which the wire 16 is inserted, and a secured part 70. The guide part 62 and the secured part 70 are separate components, and they are connected to each other. The secured part 70 includes a first shaft part 64, and a second shaft part 65 which is disposed coaxially with the first shaft part 64 in continuation to the distal end of the first shaft part 64. The guide part 62 is provided with a spherical joint 69 which offers its connection with the secured part 70, and a socket 68 which accommodates the spherical joint 69 therein is provided at the base end part of the first shaft part 64 of the secured part 70. The guide part 62 with the spherical joint 69 accommodated in the socket 68 is supported by the secured part 70 so as to be turnable around the center axis of this secured part 70.

The first shaft part 64 of the secured part 70 is formed to be slightly smaller in diameter than the shaft hole 23a of the coupling part 22a located inside, and it is loosely fitted into the shaft hole 23a. In addition, the first shaft part 64 is formed to be larger in diameter than the shaft hole 23b of the coupling part 22b located outside, and it is held in engagement with the peripheral edge part of the shaft hole 23b at its end face.

The second shaft part 65 of the secured part 70 is inserted through the shaft hole 23b of the coupling part 22b located outside. In addition, the distal end part of the second shaft part 65 protrudes out of the coupling part 22b through the shaft hole 23b. The distal end part protruding from the coupling part 22b is plastically deformed into the shape of a flat disc so as to become larger in diameter than the shaft hole 23b, thereby to be made a nip part 67.

The secured part 70 formed with the nip part 67 pinches the peripheral edge part of the shaft hole 23b of the coupling part 22b in a direction in which both the coupling parts 22a and 22b are placed one over the other, without any gap between the first shaft part 64 and the nip part 67, and it is secured to the coupling part 22b.

Although the secured part 70 is secured to the coupling part 22b of one articulation wheel 21b, the first shaft part 64 of the secured part 70 is loosely fitted into the shaft hole 23a which is formed in the coupling part 22a of the other articulation wheel 21a. Therefore, the articulation wheel 21a is turnable to the articulation wheel 21b around the first shaft part 64 of the secured part 70. In addition, the guide part 62 which is turnably supported by the secured part 70 is turnable to both the articulation wheels 21a and 21b.

In this manner, the guide part 62 of the shaft member 61 is turnable to both the two articulation wheels 21a and 21b to-be-coupled around the center axis of the secured part 70, that is, the center axis of the shaft member 61, so that when both the articulation wheels 21a and 21b have been relatively turned, the wire can be equally inflected at both the edges of the guide part 62. Thus, a force exerted on the wire 16 by the touch with the guide part 62 can be distributed, and the wear of the wire 16 can be suppressed. Further, the secured part 70 is secured to the coupling part 22b in such a manner that the peripheral edge part of the shaft hole 23b formed in the coupling part 22b of one articulation wheel 21b is pinched without any gap between the first shaft part 64 and the nip part 67, and the rattling of the shaft member 61 is prevented. Thus, the relative turning of both the articulation wheels 21a and 21b is done smoothly.

As described above, the endoscope disclosed in this specification is one including a manipulation unit, and an insertion unit which is disposed in continuation to the manipulation unit, the insertion unit containing a bending portion which has a plurality of articulation wheels connected in succession, the two adjacent ones of the articulation wheels being coupled by a shaft member so as to be relatively turnable around the shaft member on a direction crossing a center axis of the bending portion, and the bending portion being bent in such a way that a wire which leads to the manipulation unit via the plurality of articulation wheels is tractively manipulated, wherein the shaft member has a guide part formed with an insertional hole through which the wire is inserted, and at least the guide part of the shaft member is turnable around the center axis of the shaft member, to both the two articulation wheels coupled by the shaft member.

According to the endoscope stated above, the guide part of the shaft member is turnable to both the two articulation wheels to-be-coupled, so that when both the articulation wheels have been relatively turned, the wire can be equally inflected at both the edges of the guide part. Thus, a force which is exerted on the wire by the touch thereof with the guide part can be distributed, and the wear of the wire can be suppressed.

Besides, in the endoscope disclosed in this specification, each of the plurality of articulation wheels has a coupling part formed with a shaft hole through which the shaft member is inserted, and the two adjacent articulation wheels are coupled in such a manner that the shaft member is inserted through the shaft holes of the respective coupling parts placed one over the other.

Besides, in the endoscope disclosed in this specification, the shaft member has a pair of nip parts pinching at least one of the two coupling parts placed one over the other, in a direction in which the coupling parts are placed, and a gap is put in the direction of the placement, between the pair of nip parts and the coupling part to be pinched by the pair of nip parts. According to this endoscope, the shaft member is mounted without being secured to either of the two articulation wheels to-be-coupled, and the whole shaft member including the guide part becomes turnable to both the articulation wheels around its center axis. Thus, the whole shaft member including the guide part can be unitarily formed, and it can be simplified in configuration.

Besides, in the endoscope disclosed in this specification, the shaft member further has a secured part which is secured to either of the two coupling parts placed one over the other, and the guide part is separated from the secured part and is supported by this secured part so as to be turnable around the axis of the shaft member. According to this endoscope, the rattling of the shaft member can be prevented, and the relative turning of the two articulation wheels which are coupled by the shaft member is done smoothly.

What is claimed is:

1. An endoscope, comprising:
a manipulation unit; and
an insertion unit that is disposed in continuation to the manipulation unit and that includes a bending portion,
wherein the insertion unit, in the bending portion, comprises:
a plurality of articulation wheels coupled in succession; and
a plurality of shaft members, each shaft member including a guide part formed with an insertional hole through which a wire is inserted,
wherein two adjacent ones of the plurality of articulation wheels are coupled by the shaft member so as to be relatively turnable around the shaft member on a direction crossing a center axis of the bending portion,
wherein the bending portion is bent in such a way that the wire which leads to the manipulation unit via the plurality of articulation wheels is tractively manipulated,
wherein at least each guide part of the shaft member is turnable around a center axis of each shaft member, to both the two articulation wheels which are coupled by the shaft member,
wherein each of the plurality of articulation wheels comprises a coupling part formed with a shaft hole throw which the shaft member is inserted,
wherein two adjacent articulation wheels are coupled in such a way that the shaft member is inserted through the shaft holes of respective coupling parts which are placed one over another,
wherein said each shaft member includes a pair of nip parts which pinch at least one of two coupling parts placed one over another, in a direction of a placement of the coupling parts,
wherein a gap is provided, in the direction of the placement, between the pair of nip parts and the coupling part pinched by the pair of nip parts, and
wherein said each shaft member further includes a secured part which is secured to one of the two coupling parts placed one over another, and the guide part is separated from the secured part and is supported by the secured part so as to be turnable around the center axis of the shaft member.

2. The endoscope of claim 1, wherein the guide part, which is turnably supported by the secured part, is turnable to both of the two adjacent articulation wheels.

3. The endoscope of claim 1, wherein the secured part comprises:
a first shaft part; and
a second shaft part which is disposed coaxially with the first shaft part in continuation to a distal end of the first shaft part.

4. The endoscope of claim 3, wherein the secured part is secured to the coupling part of one of the two adjacent articulation wheels, and wherein the first shaft part of the secured part is fitted into the shaft hole formed in the coupling part of another one of the two adjacent articulation wheels.

5. The endoscope of claim 4, wherein said another one of the two adjacent articulation wheels is turnable to said one of the two adjacent articulation wheels around the first shaft part of the secured part.

6. The endoscope of claim 3, wherein the secured part is secured to the one of the two coupling parts such that a peripheral edge part of the shaft hole formed in the one of the two coupling parts is pinched without a gap between the first shaft part and the nip parts.

* * * * *